(12) United States Patent
Suppa et al.

(10) Patent No.: US 12,159,421 B2
(45) Date of Patent: Dec. 3, 2024

(54) METHOD OF FINDING A SET OF CORRESPONDING POINTS IN IMAGES TO BE REGISTERED, IMAGE REGISTRATION METHOD, MEDICAL IMAGE REGISTRATION SYSTEM AND SOFTWARE PROGRAM PRODUCT

(71) Applicant: OLYMPUS CORPORATION, Tokyo (JP)

(72) Inventors: Per Suppa, Hamburg (DE); Lorena Krames, Koblenz (DE)

(73) Assignee: OLYMPUS CORPORATION, Tokyo (JP)

( * ) Notice: Subject to any disclaimer, the term of this patent is extended or adjusted under 35 U.S.C. 154(b) by 327 days.

(21) Appl. No.: 17/940,347

(22) Filed: Sep. 8, 2022

(65) Prior Publication Data

US 2023/0116388 A1 Apr. 13, 2023

Related U.S. Application Data

(60) Provisional application No. 63/254,619, filed on Oct. 12, 2021.

(51) Int. Cl.
*G06T 7/33* (2017.01)
*A61B 1/00* (2006.01)
(Continued)

(52) U.S. Cl.
CPC .......... *G06T 7/337* (2017.01); *A61B 1/00009* (2013.01); *A61B 1/3132* (2013.01);
(Continued)

(58) Field of Classification Search
CPC ................ G06T 7/337; G06T 7/593; G06T 2207/10012; G06T 2207/10028;
(Continued)

(56) References Cited

U.S. PATENT DOCUMENTS

| | | | |
|---|---|---|---|
| 2008/0123927 A1* | 5/2008 | Miga | A61B 90/36 382/131 |
| 2019/0336109 A1* | 11/2019 | Pheiffer | G06T 7/37 |
| 2021/0233263 A1* | 7/2021 | Soper | G06T 7/73 |

OTHER PUBLICATIONS

Godard, C., et al., "Digging into Self-Supervised Monocular Depth Estimation", The International Conference on Computer Vision (ICCV), Oct. 2019.
(Continued)

*Primary Examiner* — Huy C Ho
(74) *Attorney, Agent, or Firm* — Scully, Scott, Murphy & Presser, P.C.

(57) ABSTRACT

A method of finding a set of corresponding points in images to be registered. According to the method, an input unit of the system receives a first user input, indicative of a reference point in an intraoperative image. A processing unit sets a reference area surrounding the reference point and converts the image data points in the reference area to a intraoperative point cloud. The input unit receives a second user input, indicative of a candidate point in a preoperative image. The processing unit sets a search area surrounding the reference point and converts the image data points in the reference area to a preoperative point cloud. By comparing geometric feature descriptors of the image data points, the processing unit finds a target point in the preoperative image corresponding to the reference point and defines the points as set of corresponding points.

14 Claims, 2 Drawing Sheets

(51) Int. Cl.
  *A61B 1/313* (2006.01)
  *G06T 7/593* (2017.01)
  *H04N 5/77* (2006.01)
(52) U.S. Cl.
  CPC .... *G06T 7/593* (2017.01); *G06T 2207/10012* (2013.01); *G06T 2207/10028* (2013.01); *G06T 2207/10081* (2013.01); *G06T 2207/10088* (2013.01); *G06T 2207/20101* (2013.01); *H04N 5/77* (2013.01)
(58) Field of Classification Search
  CPC . G06T 2207/10081; G06T 2207/10088; G06T 2207/20101; G06T 2200/04; G06T 2207/20081; G06T 2207/20084; G06T 2207/30056; G06T 7/33; A61B 1/00009; A61B 1/3132; H04N 5/77
  USPC .......................................................... 382/131
  See application file for complete search history.

(56) References Cited

OTHER PUBLICATIONS

Rusu, R.B., et al., "Fast Point Feature Histograms (FPFH) for 3D Registration", 2009 IEEE International Conference on Robotics and Automation.
Han, X.F., et al., A comprehensive review of 3D point cloud descriptors, arXiv:1802.02297v1 [cs.CV] Feb. 7, 2018.

* cited by examiner

METHOD OF FINDING A SET OF CORRESPONDING POINTS IN IMAGES TO BE REGISTERED, IMAGE REGISTRATION METHOD, MEDICAL IMAGE REGISTRATION SYSTEM AND SOFTWARE PROGRAM PRODUCT

CROSS-REFERENCE TO RELATED APPLICATION

The present application is based upon and claims the benefit of priority from U.S. Provisional Application No. 63/254,619 filed on Oct. 12, 2021, the entire contents of which is incorporated herein by reference.

BACKGROUND

Field

The present disclosure relates to a method of finding a set of corresponding points in images to be registered, an image registration method, a medical image registration system and a software program product.

Prior Art

Image registration is a technique to transform different image datasets into a common coordinate system. Image registration is used for example in medical imaging to align and overlay a preoperative image, for example a computer tomography (CT) image or a magnetic resonance (MR) image, onto an intraoperative image, for example an intraoperative laparoscopic video image. Image registration makes it possible to enrich the intraoperative image with additional information extracted from the preoperative image.

A transformation matrix is required to map the preoperative image onto the intraoperative image. To calculate the transformation matrix, it is necessary to determine multiple sets of corresponding points in the preoperative image and the intraoperative image. These sets of corresponding points each comprise a reference point in the intraoperative image and a target point in the preoperative image, with the target point corresponding to the reference point. There are a number of methods to find sets of corresponding points. For example, optical or electromagnetic tracking technologies are utilized to find the corresponding points in the respective images.

Another option is a purely image-based registration approach. In this approach, an algorithm identifies salient feature points in both images and utilizes those salient feature points as corresponding points for image registration. Salient features are for example edges, corners, anatomical landmarks and similar features visible in both images.

However, if no salient features can be found in both images, an accurate selection of corresponding points is impossible in this approach, because there is no mutually exclusive correspondence that can be determined between image data points in the images. In other words, there is more than one possible candidate point in the preoperative image that can represent the target point in the intraoperative image. An inaccurate identification of corresponding points leads to an inaccurate determination of the transformation matrix and thus to inaccurate registration results.

This problem is intensified in images of objects with smooth, texture-less surfaces, for example images of abdominal organs such as the liver. These images generally comprise more than one possible candidate point, which prevents an accurate registration.

SUMMARY

It is an object to provide a method of finding a set of corresponding points in images to be registered, an image registration method, a medical image registration system and a software program product that allow for a reliable and accurate localization of a set of corresponding points for registration.

Such object can be solved by a method of finding a set of corresponding points in images to be registered using a medical image registration system, the set of corresponding points comprising a reference point in intraoperative image data and a target point in preoperative image data, the medical image registration system comprising an input unit, a processing unit and a storage unit, the storage unit having stored thereon the preoperative image data and the intraoperative image data, wherein the input unit receives a first user input, which is indicative of a user selected image data point in the intraoperative image data, the processing unit:
sets the image data point in the intraoperative image data as the reference point in the intraoperative image data, sets a reference area comprising a plurality of image data points of the intraoperative image data including the reference point, calculates a reference depth map by calculating and assigning a depth value to every image data point in the reference area, generates an intraoperative point cloud from the reference depth map, and the input unit receives a second user input, which is indicative of a user selected image data point in the preoperative image data, the processing unit:
sets the user selected image data point in the preoperative image data as a candidate point, estimated to correspond to the reference point in the intraoperative image data, defines a search area comprising a plurality of image data points of the preoperative image data including the candidate point, calculates a search depth map by calculating and assigning a depth value to every image data point in the search area, generates a preoperative point cloud from the search depth map, calculates and assigns a geometric feature descriptor to every image data point in the intraoperative point cloud and to every image data point in the preoperative point cloud, wherein the geometric feature descriptor of an image data point is indicative of at least one geometric relation of said image data point to at least one of its neighboring image data points, compares the geometric feature descriptor of the reference point with the geometric features descriptors of at least two of the image data points in the preoperative point cloud, sets an image data point in the preoperative point cloud, whose geometric feature descriptor best matches the geometric feature descriptor of the reference point, as the target point, and assigns the reference point in the intraoperative image data and the target point in the preoperative image data as the set of corresponding points.

The method combines an automatic image-based registration with a manual registration approach. The user selects an image data point in the intraoperative image data and an image data point in the preoperative image data, which the user assumes correspond to each other. This rough estimation is used to reduce the amount of candidate points from which the target point is chosen, as only image data points in the search area are considered possible target points. The target point can be any image data point in the search area, even the candidate point itself.

The reference point is part of the plurality of image data points of the reference area. Likewise, the candidate point is part of the plurality of image data points of the search area. According to an embodiment, the reference area can be a contiguous area surrounding and including the reference point. According to another embodiment, the search area can comprise a contiguous area surrounding and including the candidate point. The image data points in the reference area can comprise all image data points inside a first radius around the reference point. The image data points in the search area can comprise all image data points inside a second radius around the candidate point. The first radius can equal the second radius.

A depth map can comprise information about a distance of each image data point to a plane. The reference depth map can comprise information indicative of a distance of the image data points in the reference area from a viewpoint or a viewing plane. The search depth map can comprise information indicative of a distance of the image data points in the search area from a viewpoint or a viewing plane. The reference depth map and/or the search depth map can comprise a depth value for each image data point.

Three dimensional coordinates, such as cartesian coordinates, can be assigned to every image data point of the intraoperative point cloud and/or the preoperative point cloud.

An image data point can be a pixel and/or a voxel.

The geometric feature descriptor can indicate the geometric relation of an image data point to its neighboring image data points. Such approach can allow to accurately distinguish between image data points that otherwise might seem quite similar. Thus, a comparison of the geometric feature descriptors of the reference point and the image data points in the preoperative point cloud can be a precise and fast way to find the target point and assign the set of corresponding points.

The processing unit can compare the geometric feature descriptor of the reference point with the geometric features descriptors of all of the image data points in the preoperative point cloud.

The geometric feature descriptor of at least one image data point in the intraoperative point cloud and/or the preoperative point cloud can be indicative of a surface normal of said image data point and/or a distance to at least one of its neighboring image data points and/or a direction to at least one of its neighboring image data points. The geometric feature descriptor of all image data points in the intraoperative point cloud and/or the preoperative point cloud can be indicative of a surface normal of said image data point and/or a distance to at least one of its neighboring image data points and/or a direction to at least one of its neighboring image data points.

The surface normal of an image data point, the distance to at least one of its neighboring image data points and the direction to at least one of its neighboring image data points are geometric relations, which can be well suited to distinguish the image data point.

The medical image registration system can comprise a laparoscope, wherein the intraoperative image data is recorded by the laparoscope, such as intraoperative laparoscopic video data, and transmitted to the storage unit.

The application of the method to laparoscopic image data can allow for a precise and fast registration of the images captured by a laparoscope with preoperative image data from a CT scanner of a magnetic resonance imaging device. The intraoperative image data can be intraoperative laparoscopic video data, which allows for image registration of the video data from the laparoscope during an operation.

The laparoscope can be a stereo laparoscope, wherein the intraoperative image data being recorded by the stereo laparoscope is stereo intraoperative image data, wherein the stereo intraoperative image data can be indicative of a depth value of each image data point of the intraoperative image data, wherein the processing unit calculates the reference depth map by calculating the depth value of every image data point in the reference area by utilizing the stereo intraoperative image data.

A stereo laparoscope is an easy way of assigning a depth value to image data points. In this way, the reference depth map can be calculated quickly with the stereo intraoperative image data. The stereo intraoperative image data can be stereo intraoperative video data.

Additionally, or alternatively, the processing unit can generate the reference depth map and/or the search depth map by utilizing a deep learning network for depth estimation, wherein the deep learning network for depth estimation calculates the depth value of every image data point with a deep learning algorithm, wherein the deep learning network for depth estimation can be stored on the storage unit.

A deep learning network for depth estimation and a deep learning algorithm is for example known from "C. Godard and O. Mac Aodha and M. Firman and G. J. Brostow, Digging into Self-Supervised Monocular Depth Prediction. The International Conference on Computer Vision (ICCV), October 2019". Such a deep learning network is capable of calculating and assigning a depth value to image data points in a two dimensional image after being trained with appropriate image data.

The processing unit can calculate a geometric feature descriptor for every image data point in the intraoperative point cloud and for every image data point in the preoperative point cloud via a feature descriptor program, such as a fast point feature histogram descriptor program, wherein the feature descriptor program can be stored on the storage unit.

A geometric feature descriptor can represent the geometric relations at a point in relation to neighboring points. A feature descriptor program is a program, which can calculate the geometric relations at the point quickly and efficiently. An example for a 3D point cloud descriptor program is the fast point feature histogram descriptor program known from "R. B. Rusu, N. Blodow and M. Beetz, Fast Point Feature Histograms (FPFH) for 3D registration, 2009 IEEE International Conference on Robotics and Automation". Other types of 3D point cloud descriptor are for example a Fast Point Feature Histogram Descriptor, a Signature of Histogram of Orientation (SHOT) descriptor or a Spin Image descriptor. An overview of different types of 3D point cloud descriptor program can be found in "X. F. Han, J. S. Jin, J. Xie, M. J. Wang, W. Jiang, A comprehensive review of 3D point cloud descriptors, arXiv:1802.02297v1 [cs.CV] 7 Feb. 2018".

The preoperative image data can be recorded with a preoperative image capturing device before an operation and the intraoperative image data can be recorded with an intraoperative image capturing device during the operation, the preoperative image capturing device transmitting the preoperative image data to the storage unit and the intraoperative image data to the storage unit.

The intraoperative image capturing device can be for example an endoscope or laparoscope and the preoperative image capturing device can be for example a CT scanner or a magnetic resonance imaging device. The medical image registration system can comprise the intraoperative image capturing device and/or the preoperative image capturing device.

Such object can be further solved by an image registration method to align a preoperative image with an intraoperative image via a medical image registration system, the medical image registration system comprising an input unit, a processing unit and a storage unit,
- wherein the medical image registration system assigns at least three different sets of corresponding points with the method according to any of the previously described embodiments,
- wherein the processing unit calculates a transformation matrix based on the sets of corresponding points, wherein the transformation matrix is configured to map the preoperative image data onto the intraoperative image data when applied to the preoperative image data,
- wherein the processing unit spatially aligns the preoperative image data with the intraoperative image data by applying the transformation matrix to the preoperative image data.

The image registration method can employ the method of finding a set of corresponding points to reliably and accurately find multiple sets of corresponding points, which can be utilized to calculate the transformation matrix and register the preoperative image data with the intraoperative image data.

Such object can be further solved by a medical image registration system to align a preoperative image with an intraoperative image, the medical image registration system comprising an input unit, a processing unit and a storage unit, the storage unit having stored thereon preoperative image data and intraoperative image data, wherein the medical image registration system can be configured to carry out a method according to any of the previous embodiments.

The same or similar advantages apply to the medical image registration system as were previously mentioned with respect to the method of finding a set of corresponding points and the image registration method.

Such object can be further solved by a software program product comprising program code means for a medical imaging system according to the previously described embodiment, comprising a control program component that is executed in the processing unit of the medical imaging system, characterized in that the control program component can be configured to carry out a method according to any of the previously described embodiments.

The same or similar advantages apply to the software program product as were previously mentioned with respect to the medical image registration system, the method of finding a set of corresponding points and the image registration method.

BRIEF DESCRIPTION OF THE DRAWINGS

Further characteristics will become apparent from the description of the embodiments together with the claims and the included drawings. Embodiments can fulfill individual characteristics or a combination of several characteristics.

The embodiments are described below, without restricting the general intent of the invention, based on the exemplary embodiments, wherein reference is made expressly to the drawings with regard to the disclosure of all details that are not explained in greater detail in the text. In the drawings.

In the drawings, the same or similar types of elements or respectively corresponding parts are provided with the same reference numbers in order to prevent the item from needing to be reintroduced.

DETAILED DESCRIPTION

Figure 1:
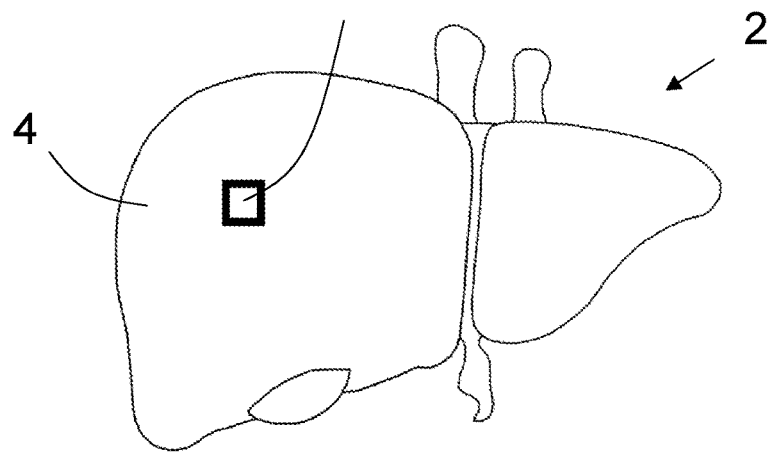
FIG. 1 illustrates a schematic simplified representation of an intraoperative image of a liver.

FIG. 1 shows a schematic representation of an intraoperative image of an organ 2, in this case a liver. The intraoperative image data of the intraoperative image is for example captured with a laparoscope and can be part of intraoperative laparoscopic video data. The intraoperative image can be registered with a preoperative image to spatially align both images, which makes it possible to enrich the intraoperative image with additional information. This requires a number of sets of corresponding points in both images, each set comprising a reference point 10 in the intraoperative image and a target point in the preoperative image, which are usually detected by an algorithm. To properly align the images, the target point has to correspond exactly to the reference point 10. In FIG. 1, the reference point 10 is illustrated as a square.

Figure 2:
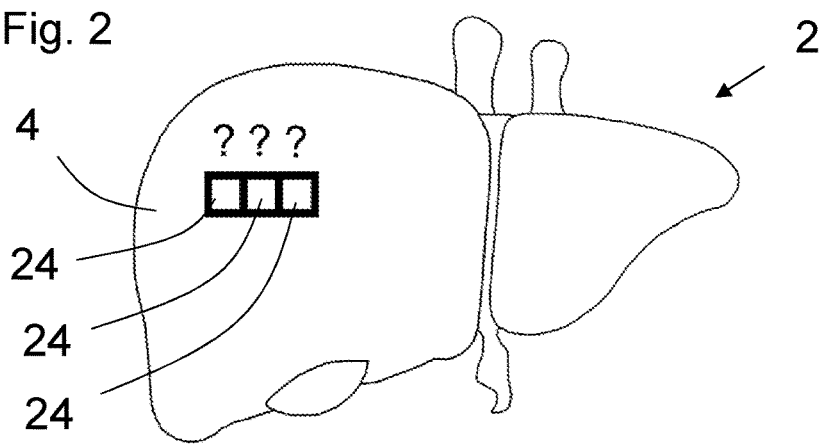
FIG. 2 illustrates a schematic simplified representation of a preoperative image of a liver.

The algorithm utilizes salient features like corners or anatomic features in the images as corresponding points. However, finding the set of corresponding points is difficult if there are no salient features visible in the images. This is the case with the surface 4 of the liver, which is largely texture-less, making it difficult to identify the target point, as is exemplified in FIG. 2. FIG. 2 shows a schematic representation of a preoperative image of the organ 2, for example a CT image. Due to the texture-less surface 4 of the organ 2, it is not possible to reliably identify the image data point 24 in the preoperative image data, which corresponds to the reference point 10 in the intraoperative image data, because there are multiple image data points 24, which all exhibit similar geometric features as the reference point 10. In other words, there is no mutually exclusive correspondence between the reference point 10 and a single image data point 24 in the preoperative image data.

Figure 3:
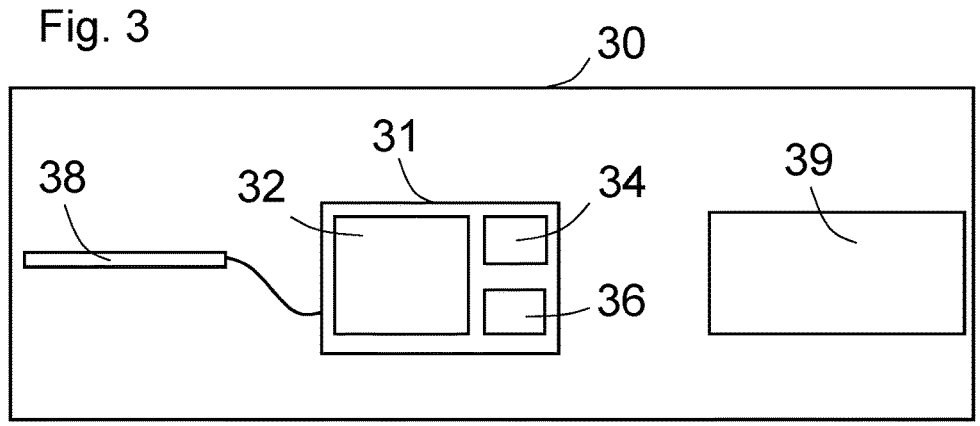
FIG. 3 illustrates a schematic simplified representation of a medical image registration system.

To solve this problem, a method of finding a set of corresponding points is executed by a medical image registration system 30, which is shown in FIG. 3. The medical image registration system 30 comprises an input unit 32, a processing unit 34 and a storage unit 36, which are for example implemented in a workstation 31, a computer or a medical device. The input unit 32 is for example a touchscreen that depicts the intraoperative image and/or the preoperative image and allows a user to select an image data point on the screen as reference point 10 or candidate point. Alternatively, the input unit 32 can be a mouse or a keyboard or a similar input device. On the storage unit 36, which is for example a computer memory, the preoperative image data and the intraoperative image data is being stored. The processing unit 34 is configured to carry out the method of finding a set of corresponding points and image registration methods. For example, the processing unit 34 is a CPU or a similar device. The medical image registration system 30 can also comprise an intraoperative image capturing device 38, for example a laparoscope, and a preoperative image capturing device 39, for example a CT scanner.

Figure 4:
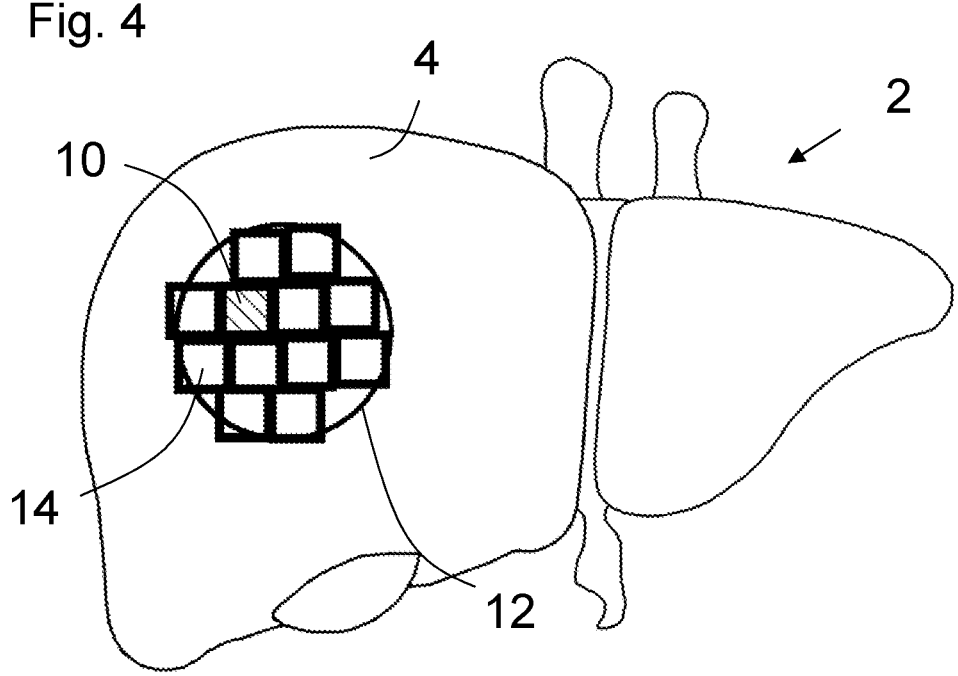
FIG. 4 illustrates a schematic simplified representation of an intraoperative image of a liver with a reference point and a reference area.
Figure 5:
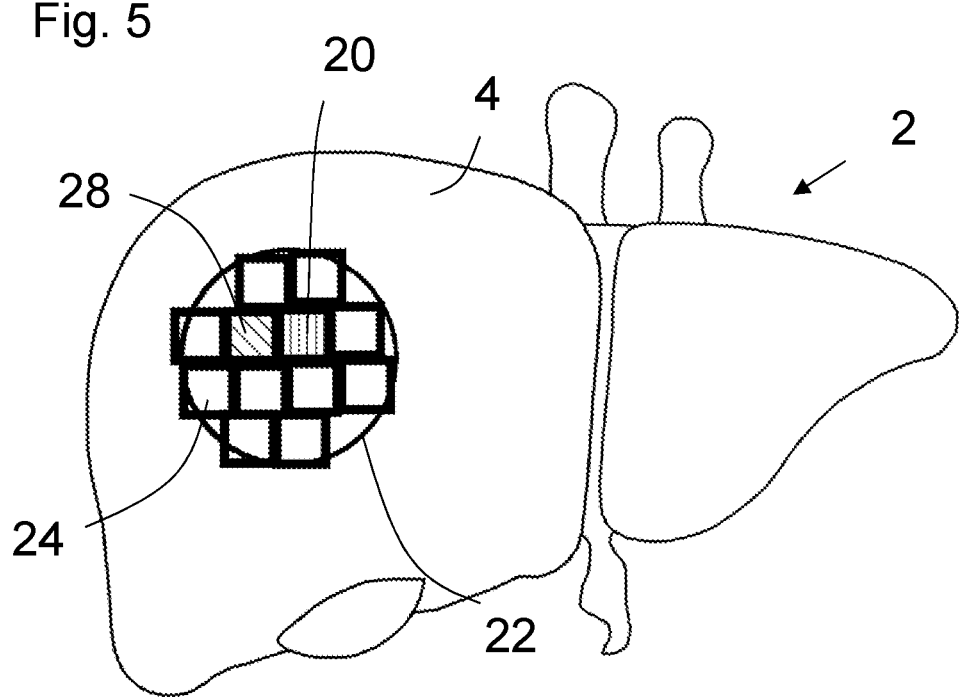
FIG. 5 illustrates a schematic simplified representation of a preoperative image of a liver with a candidate point, a search area and a target point.

FIG. 4 shows an intraoperative image of the organ 2 utilized by the method of finding a set of corresponding points using the medical image registration system 30 and FIG. 5 shows a preoperative image of the organ 2 utilized by the method of finding a set of corresponding points using the medical image registration system 30. In the following, an exemplary embodiment of a method of finding a set of corresponding points is explained by making use of FIGS. 4 and 5.

A user, for example a surgeon, selects the target point 28 in the intraoperative image data by entering a first user input into the input unit 32. The reference point 10 is indicated in FIG. 4 by diagonal lines. The input unit 32 receives the first user input and the processing unit 34 sets it as the target point 28. Then, the processing unit 34 sets a reference area 12 comprising a plurality of image data points 14 of the intraoperative image data including the reference point 10. To simplify understanding, in FIG. 4 only one of the image data points 14, which are illustrated as squares, is provided with a reference sign, even though all squares, including the reference point 10 itself, are image data points 14. According to an embodiment, the reference area 12 comprises a contiguous area surrounding and including the reference point 10. For example, the reference area 12 comprises every image data point 14 in a specified radius around the reference point 10. In FIG. 4, the reference area 12 is depicted as a circle including but not centered on reference point 10.

Then, the processing unit 34 calculates a reference depth map of the reference area 12 by calculating and assigning a depth value to every image data point 14 in the reference area 12. The depth values are for example obtained by a stereo laparoscope or a deep learning network for depth estimation. From the reference depth map an intraoperative point cloud is generated by the processing unit 32. The intraoperative point cloud includes coordinate information for every image data point 14 in the intraoperative point cloud.

The surgeon also selects a candidate point 20 in the preoperative image data by entering a second user input into the input unit 32. The candidate point 20 is indicated in FIG. 5 by vertical lines. The surgeon believes the candidate point 20 to roughly correspond to the reference point 10, even though in reality the target point 28, indicated by diagonal lines, is the correct corresponding point. The precise selection of the correct candidate point 20 might for example be impeded by the fact, that the surgeon has to select an image data point 24 on a two-dimensional screen that depicts a three dimensional organ 4. The input unit 32 receives the second user input and the processing unit 34 sets it as the candidate point 20.

The processing unit 34 sets a search area 22 comprising a plurality of image data points 24 of the preoperative image data including the candidate point 20. To increase the clarity of FIG. 5, only one of the image data points 24, which are illustrated as squares, is provided with a reference sign. Nonetheless, all squares in FIG. 5, including the candidate point 20 and the target point 28, are image data points 24. According to an embodiment, the search area 22 comprises a contiguous area surrounding and including the candidate point 20. For example, the search area 22 comprises the image data points 24 in a specified radius around the candidate point 20. In FIG. 5, the search area 22 is depicted as a circle including but not centered on candidate point 20.

The processing unit 34 calculates a search depth map of the search area 22 by calculating a depth value to every image data point in the search area 22. The depth values are for example obtained by a deep learning network for depth estimation. From the search depth map a preoperative point cloud is generated by the processing unit 34. The preoperative point cloud includes coordinate information for every image data point 24 in the preoperative point cloud.

Afterwards, the processing unit 34 calculates and assigns a geometric feature descriptor to every image data point 14 in the intraoperative point cloud and to every image data point 24 in the preoperative point cloud. The geometric feature descriptor is indicative of at least one geometric relation of said image data point 14, 24 to at least one of its neighboring image data points 14, 24. It comprises at least one geometric feature, for example a surface normal of the image data point 14, 24, a distance to at least one of its neighboring image data points 14, 24 or a direction to at least one of its neighboring image data points 14, 24. Thus, the geometric feature descriptor of an image data point 14, 24 distinguishes it from other image data points 14, 24, even when they might look similar if viewed in isolation.

Then, the processing unit 34 compares the geometric feature descriptor of the reference point 10 with the geometric features descriptors of the image data points 24 in the preoperative point cloud. This allows to reliably identify the target point 28 as the image data point 24, whose geometric feature descriptor best matches the geometric feature descriptor of the reference point 10. In FIG. 5, the method corrects the user selection of the candidate point 20 to select the target point 28 instead, which truly corresponds to the reference point 10. By restricting the selection of the target point 28 to the preoperative point cloud, image data points outside the search area 22, whose geometric feature descriptor coincidentally resemble the geometric feature descriptor of the reference point 10, cannot be accidentally chosen as target point 28. In this way, the accuracy of the method is increased.

Finally, the reference point 10 in the intraoperative image data and the target point 28 in the preoperative image data are assigned as the set of corresponding points.

This method can be repeated to obtain different sets of corresponding points, which are subsequently used to calculate a transformation matrix. The transformation matrix allows to spatially align the preoperative image with the intraoperative image. In this way, a reliable and accurate image registration is achieved.

While there has been shown and described what is considered to be embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCES 2 organ
4 surface 10 reference point
12 reference area
14 image data point
20 candidate point
22 search area
24 image data point
28 target point
30 medical image registration system
31 workstation
32 input unit
34 processing unit
36 storage unit
38 intraoperative image capturing device
39 preoperative image capturing device

What is claimed is:

1. A method of finding a set of corresponding points in images to be registered using a medical image registration system, the set of corresponding points comprising a reference point in intraoperative image data and a target point in preoperative image data, wherein the method comprises:
receiving a first user input indicative of a user selected image data point in the intraoperative image data,
setting the image data point in the intraoperative image data as the reference point,
setting a reference area comprising a plurality of image data points of the intraoperative image data including the reference point,
calculating a reference depth map by calculating and assigning a depth value to every image data point in the reference area,
generating an intraoperative point cloud from the reference depth map,
receiving a second user input indicative of a user selected image data point in the preoperative image data,
setting the user selected image data point in the preoperative image data as a candidate point, estimated to correspond to the reference point in the intraoperative image data,
defining a search area comprising a plurality of image data points of the preoperative image data including the candidate point,
calculating a search depth map by calculating and assigning a depth value to every image data point in the search area,
generating a preoperative point cloud from the search depth map,
calculating and assigning a geometric feature descriptor to every image data point in the intraoperative point cloud and to every image data point in the preoperative point cloud, wherein the geometric feature descriptor of an image data point is indicative of at least one geometric relation of said image data point to at least one of its neighboring image data points,
comparing the geometric feature descriptor of the reference point with the geometric features descriptors of at least two of the image data points in the preoperative point cloud,
setting an image data point in the preoperative point cloud, whose geometric feature descriptor best matches the geometric feature descriptor of the reference point, as the target point, and
assigning the reference point in the intraoperative image data and the target point in the preoperative image data as the set of corresponding points.

2. The method according to claim 1, wherein the geometric feature descriptor of at least one of the image data point in the intraoperative point cloud and the preoperative point cloud is indicative of a surface normal of one or more of the image data point and a distance to at least one of its neighboring image data points and a direction to at least one of its neighboring image data points.

3. The method according to claim 1, wherein the method further comprises recording the intraoperative image data by a laparoscope and storing the recorded intraoperative image data.

4. The method according to claim 3, wherein the intraoperative image data comprises the intraoperative image data.

5. The method according to claim 3, wherein the intraoperative image data stereo intraoperative image data, the stereo intraoperative image data being indicative of a depth value of each image data point of the intraoperative image data, the method comprising calculating the reference depth map by calculating the depth value of every image data point in the reference area by utilizing the stereo intraoperative image data.

6. The method according to claim 3, wherein the method comprises generating one or more of the reference depth map and the search depth map by utilizing a deep learning network for depth estimation, wherein the deep learning network for depth estimation is configured to calculate the depth value of every image data point with a deep learning algorithm.

7. The method according to claim 6, further comprising storing the deep learning network for depth estimation.

8. The method according to claim 1, wherein the method comprises calculating a geometric feature descriptor for every image data point in the intraoperative point cloud and for every image data point in the preoperative point cloud via a feature descriptor program.

9. The method according to claim 8, wherein the geometric feature descriptor comprises a fast point feature histogram descriptor program.

10. The method according to claim 8, further comprising storing the feature descriptor program.

11. The method according to claim 1, wherein the method comprises:
capturing the preoperative image data with a preoperative image capturing device before an operation;
capturing the intraoperative image data with a intraoperative image capturing device during the operation;
receiving the preoperative image data; and
receiving the intraoperative image data to.

12. An image registration method to align a preoperative image with an intraoperative image via a medical image registration system, the method comprising:
assigning at least three different sets of corresponding points with the method according to claim 1,
calculating a transformation matrix based on the at least three different sets of corresponding points, wherein the transformation matrix is configured to map the preoperative image data onto the intraoperative image data when applied to the preoperative image data, and
spatially aligning the preoperative image data with the intraoperative image data by applying the transformation matrix to the preoperative image data.

13. A medical image registration system to align a preoperative image with an intraoperative image, the medical image registration system comprising:
a processor, the processor being configured to:
receive a first user input indicative of a user selected image data point in the intraoperative image data,
set the image data point in the intraoperative image data as the reference point, set a reference area comprising a plurality of image data points of the intraoperative image data including the reference point, calculate a reference depth map by calculating and assigning a depth value to every image data point in the reference area, generate an intraoperative point cloud from the reference depth map, receive a second user input indicative of a user selected image data point in the preoperative image data, set the user selected image data point in the preoperative image data as a candidate point, estimated to correspond to the reference point in the intraoperative image data, define a search area comprising a plurality of image data points of the preoperative image data including the candidate point, calculate a search depth map by calculating and assigning a depth value to every image data point in the search area, generate a preoperative point cloud from the search depth map, calculating and assigning a geometric feature descriptor to every image data point in the intraoperative point cloud and to every image data point in the preoperative point cloud, wherein the geometric feature descriptor of an image data point is indicative of at least one geometric relation of said image data point to at least one of its neighboring image data points, compare the geometric feature descriptor of the reference point with the geometric features descriptors of at least two of the image data points in the preoperative point cloud, set an image data point in the preoperative point cloud, whose geometric feature descriptor best matches the geometric feature descriptor of the reference point, as the target point, and assign the reference point in the intraoperative image data and the target point in the preoperative image data as the set of corresponding points.

14. Non-transitory computer-readable storage medium storing instructions that cause a computer to:

receive a first user input indicative of a user selected image data point in the intraoperative image data, set the image data point in the intraoperative image data as the reference point, set a reference area comprising a plurality of image data points of the intraoperative image data including the reference point, calculate a reference depth map by calculating and assigning a depth value to every image data point in the reference area, generate an intraoperative point cloud from the reference depth map, receive a second user input indicative of a user selected image data point in the preoperative image data, set the user selected image data point in the preoperative image data as a candidate point, estimated to correspond to the reference point in the intraoperative image data, define a search area comprising a plurality of image data points of the preoperative image data including the candidate point, calculate a search depth map by calculating and assigning a depth value to every image data point in the search area, is generate a preoperative point cloud from the search depth map, calculating and assigning a geometric feature descriptor to every image data point in the intraoperative point cloud and to every image data point in the preoperative point cloud, wherein the geometric feature descriptor of an image data point is indicative of at least one geometric relation of said image data point to at least one of its neighboring image data points, compare the geometric feature descriptor of the reference point with the geometric features descriptors of at least two of the image data points in the preoperative point cloud, set an image data point in the preoperative point cloud, whose geometric feature descriptor best matches the geometric feature descriptor of the reference point, as the target point, and assign the reference point in the intraoperative image data and the target point in the preoperative image data as the set of corresponding points.

* * * * *